(12) United States Patent
Kuras et al.

(10) Patent No.: US 6,585,739 B2
(45) Date of Patent: Jul. 1, 2003

(54) APPARATUS FOR ATTACHING A CRANIAL FLAP

(75) Inventors: James Michael Kuras, Macedonia, OH (US); Charles Fredrick Birchall, Jr., Mentor, OH (US)

(73) Assignee: Medtronic PS Medical, Inc., Goleta, CA (US)

( * ) Notice: Subject to any disclaimer, the term of this patent is extended or adjusted under 35 U.S.C. 154(b) by 155 days.

(21) Appl. No.: 09/761,229

(22) Filed: Jan. 16, 2001

(65) Prior Publication Data

US 2002/0095156 A1 Jul. 18, 2002

(51) Int. Cl.⁷ .................... A61B 17/56; A61B 17/58; A61F 2/30
(52) U.S. Cl. .................. 606/72; 606/70; 606/71; 623/17.19
(58) Field of Search .................. 606/72, 70, 71, 606/104, 151; 623/17.19; 411/338, 458, 460, 487, 493, 497, 499; 81/424.5, 426.5; 403/1, 43, 409.1

(56) References Cited

U.S. PATENT DOCUMENTS

| | | | |
|---|---|---|---|
| 5,501,685 A | 3/1996 | Spetzler | |
| 5,549,620 A | 8/1996 | Bremer | |
| 5,669,912 A | 9/1997 | Spetzler | |
| 5,707,373 A | 1/1998 | Sevrain et al. | |
| 5,800,436 A | 9/1998 | Lerch | |
| 5,882,351 A | * 3/1999 | Fox | 606/60 |
| 5,916,217 A | 6/1999 | Manthrop et al. | |
| 5,954,723 A | 9/1999 | Spetzler | |
| 5,968,098 A | 10/1999 | Winslow | |
| 5,976,141 A | 11/1999 | Haag et al. | |
| 6,022,351 A | * 2/2000 | Bremer et al. | 606/72 |
| 6,068,631 A | 5/2000 | Lerch | |
| 6,090,999 A | 7/2000 | Bruce et al. | |
| 6,099,530 A | * 8/2000 | Simonian et al. | 606/151 |
| 6,126,663 A | 10/2000 | Hair | |
| 6,168,596 B1 | * 1/2001 | Wellisz et al. | 606/151 |
| 6,190,389 B1 | * 2/2001 | Wellisz et al. | 606/69 |
| 6,197,030 B1 | * 3/2001 | Pham | 24/265 B |
| 6,287,310 B1 | * 9/2001 | Fox | 606/60 |
| 6,328,743 B2 | 12/2001 | Lerch | |
| 6,355,044 B1 | * 3/2002 | Hair | 606/72 |
| 6,379,361 B1 | * 4/2002 | Beck et al. | 606/104 |
| 6,379,363 B1 | * 4/2002 | Herrington et al. | 606/104 |

FOREIGN PATENT DOCUMENTS

| | | |
|---|---|---|
| DE | 29614921 | 10/1996 |
| DE | 29614923 | 10/1996 |

* cited by examiner

Primary Examiner—Henry Bennett
Assistant Examiner—Kathryn Ferko
(74) Attorney, Agent, or Firm—Tarolli, Sundheim, Covell & Tummino L.L.P.

(57) ABSTRACT

An apparatus for attaching a cranial flap (20) to a skull (10) includes an attachment device (40) having relatively movable first and second members (42 and 44). The first member (40) has first and second surfaces (56 and 58) for engaging first and second kerf edges (24 and 26), respectively, of a kerf (22). The second member (44) has third and fourth surfaces (120 and 122) for engaging the first and second kerf edges (24 and 26), respectively. A shaft (46) connects the first and second members (42 and 44). The shaft (46) is attached to the second member (44) and extends through an opening (114) in the first member (42). The attachment device (40) is positionable in the kerf (22) and movable from a first condition in which the first and second members (42 and 44) are not engaged with the kerf edges (24 and 26) to a second condition in which the attachment device is wedged in the kerf between the first and third surfaces (56 and 120) and the first kerf edge (24) and between the second and fourth surfaces (58 and 122) and the second kerf edge (26)

16 Claims, 5 Drawing Sheets

APPARATUS FOR ATTACHING A CRANIAL FLAP

TECHNICAL FIELD

The present invention is directed to an apparatus for attaching a cranial flap to a skull, from which the cranial flap was removed, during surgery.

BACKGROUND OF THE INVENTION

Surgical operations involving the human skull, such as brain surgery or craniofacial surgery, require that a section of the skull be removed. Typically, a number of burr holes are first drilled into the skull and which outline the section of the skull to be removed. A cutting tool is then inserted into one of the burr holes and a cut, or osteotomy, is made from one burr hole to then next burr hole until a loop is completed. The loop of osteotomies forms an opening in the skull and defines the section of the skull to be removed. The section of the skull to be removed is commonly referred to as a cranial flap. Because the blade on the cutting tool typically has a width of 1–3 mm, a kerf of that width is formed between the opening in the skull and the cranial flap. Due to the width of the kerf, the periphery of the cranial flap is smaller than the opening in the skull.

When the surgical procedure inside the skull is complete, the cranial flap must be replaced in the opening in the skull and re-attached to the skull. A number of methods and attachment devices are known for re-attaching the cranial flap to the skull. One known method uses stainless steel wire as a suture material for wiring the cranial flap and the skull together. Some of the known devices include plates and associated screws made from either titanium or a bioabsorbable polymer. Other known devices employ rivet-type fasteners made of titanium or a biocompatible polymer such as acetyl resin.

One of the disadvantages of several of the known attachment devices is that a portion of the device rests on top of, and thus protrudes from, the outer surface of the skull, resulting in visible and unsightly bumps under the patient's skin. Another disadvantage of the known rivet-type fasteners is that a portion of the fastener remains in contact with the dura, as it is generally believed that such contact with the dura could be potentially harmful. Thus, it is desirable to provide an attachment device which is disposed entirely within the kerf and thus does not contact the dura nor protrude beyond the outer surface of the skull.

SUMMARY OF THE INVENTION

The present invention is an apparatus for attaching a cranial flap to a skull during surgery. The cranial flap and the skull are spaced apart by a kerf defined by a first kerf edge on the cranial flap and an oppositely disposed second kerf edge on the skull. The apparatus comprises at least one attachment device comprising first and second members that are movable relative to each other along an axis. The first member has oppositely disposed first and second surfaces for engaging the first and second kerf edges, respectively. The first member further includes an opening extending along the axis. The second member has oppositely disposed third and fourth surfaces for engaging the first and second kerf edges, respectively. A shaft member connects the first and second members. The shaft member is attached to the second member and extends through the opening in the first member. The at least one attachment device is positionable in the kerf and movable from a first condition in which the first surface on the first member and the third surface on the second member are not engaged with the first kerf edge and the second surface on the first member and the fourth surface on the second member are not engaged with the second kerf edge to a second condition in which the at least one attachment device is wedged in the kerf by circumferential pressure and frictional engagement between the first and third surfaces and the first kerf edge and by circumferential pressure and frictional engagement between the second and fourth surfaces and the second kerf edge to thereby attach the cranial flap to the skull and prevent the cranial flap from moving relative to the skull.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF PREFERRED EMBODIMENTS

Figure 1:
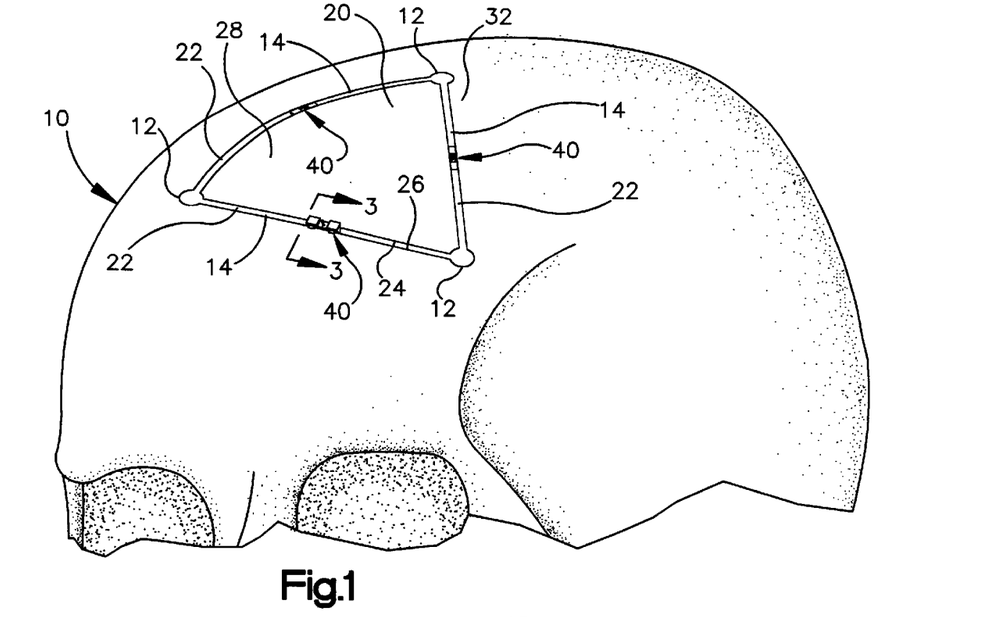
FIG. 1 is a perspective view of a portion of a skull illustrating an apparatus for attaching a cranial flap to the skull in accordance with the present invention.

The present invention is directed to an apparatus for attaching a cranial flap to a skull, from which the cranial flap was removed, during surgery. As representative of the present invention, FIG. 1 illustrates a human skull 10 on which surgery is being performed.

To access a particular region inside the skull 10, the surgeon drills a number of burr holes 12 in the skull. A cutting tool (not shown) is then inserted into a first one of the burr holes 12 and a cut 14 is made in the skull 10 from the first one of the burr holes to another of the burr holes. Additional cuts 14 in the skull 10 are made between the other burr holes 12 until a loop is completed. In the representative illustration of FIG. 1, there are three cuts 14. It should be apparent that more than three burr holes 12 and three cuts 14 may be made at the discretion of the surgeon.

The loop of cuts 14 in the skull 10 forms an opening (not numbered) in the skull and defines a cranial flap 20 to be removed. While making the cuts 14, the width of the cutting tool forms a kerf 22 between the cranial flap 20 and the skull 10. Hence, the cranial flap 20 is slightly smaller than the opening in the skull 10. When the surgical procedure inside the skull 10 is complete, the cranial flap 20 is replaced in the opening in the skull and secured to the skull as described below.

The kerf 22 between the cranial flap 20 and the skull 10 is defined by a first kerf 24 edge on the cranial flap and an oppositely disposed second kerf edge 26 on the skull. The first kerf edge 24 extends between inner and outer surfaces 28 and 30 (FIG. 3) of the cranial flap. The second kerf edge 26 extends between inner and outer surfaces 32 and 34 of the skull.

Figure 2:
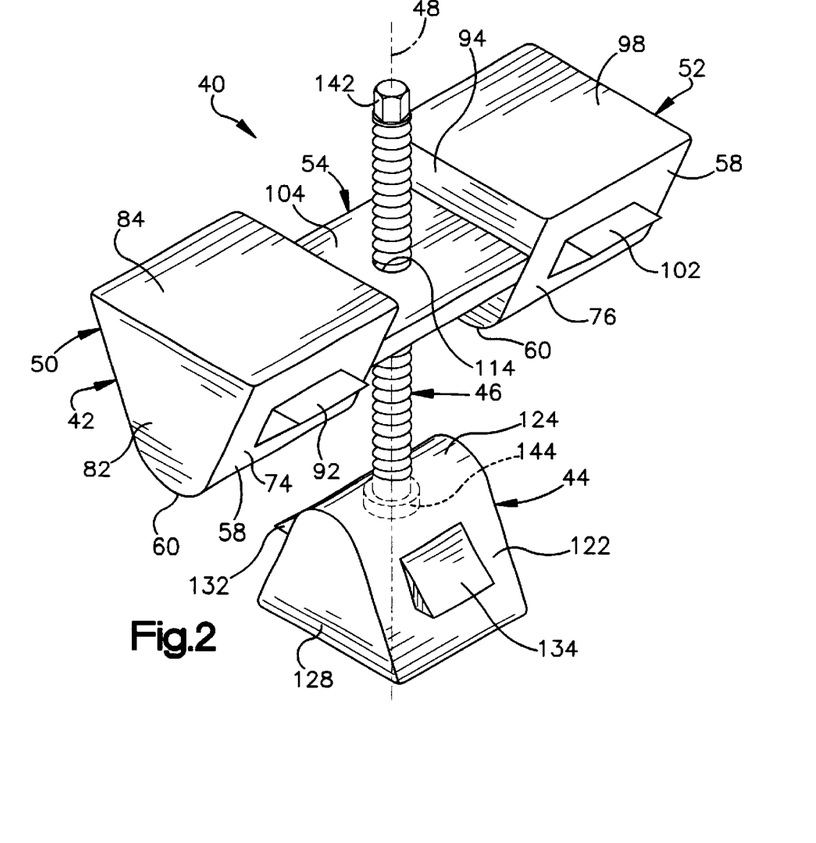
FIG. 2 is a perspective view of the apparatus for attaching a cranial flap in accordance with a first embodiment of the present invention.

A first embodiment of an attachment device 40 for securing the cranial flap 20 to the skull 10 is illustrated in FIG. 2. The attachment device 40 according to the first embodiment is designed to fit into the kerf 22 that extends between two of the burr holes 12 in the skull 10, as is described further below. The attachment device 40 comprises relatively movable first and second members 42 and 44 connected by a shaft member 46 that extends along an axis 48. The first and second members 42 and 44 and the shaft member 46 of the attachment device 40 are made of a biocompatible metal, such as titanium or a titanium alloy. It is contemplated, however, that one or more of the components of the attachment device 40 could alternatively be made of acetal plastic.

The first member 42 includes first and second sections 50 and 52 (FIG. 2) that are connected by a bridge section 54. Each of the first and second sections 50 and 52 of the first member 42 has a wedge shape defined by first and second surfaces 56 (FIG. 3) and 58 (FIG. 2) that extend at diverging angles relative to the axis 48. The first and second surfaces 56 and 58 on each of the first and second sections 50 and 52 of the first member are joined by an arcuate end surface 60 (FIG. 2).

A first portion 70 (FIG. 5) of the first surface 56 extends across the first section 50 of the first member 42 and a second portion 72 of the first surface extends across the second section 52 of the first member. Similarly, a first portion 74 (FIG. 2) of the second surface extends across the first section 50 of the first member 42 and a second portion 76 of the second surface extends across the second section 52 of the first member.

The first section 50 of the first member 42 has generally parallel inner and outer surfaces 80 and 82 (FIG. 5) that extend between the first portion 70 of the first surface 56 and the first portion 74 of the second surface 58. The first section 50 includes a generally planar upper surface 84 that is disposed opposite the arcuate end surface 60.

The first section 50 of the first member 42 further includes a first tooth 90 that projects radially outward from the first portion 70 of the first surface 56. A second tooth 92 (FIG. 2) projects radially outward from the first portion 74 of the second surface 58 of the first section 50 of the first member 42.

The second section 52 of the first member 42 has generally parallel inner and outer surface surfaces 94 and 96 (FIG. 5) that extend between the second portion 72 of the first surface 56 and the second portion 76 of the second surface 58. The second section 52 includes a generally planar upper surface 98 that is disposed opposite the arcuate end surface 60.

The second section 52 of the first member 42 further includes a third tooth 100 that projects radially outward from the second portion 72 of the first surface 56. A fourth tooth 102 (FIG. 2) projects radially outward from the second portion 76 of the second surface 58 of the second section 52 of the first member 42.

Figure 5:
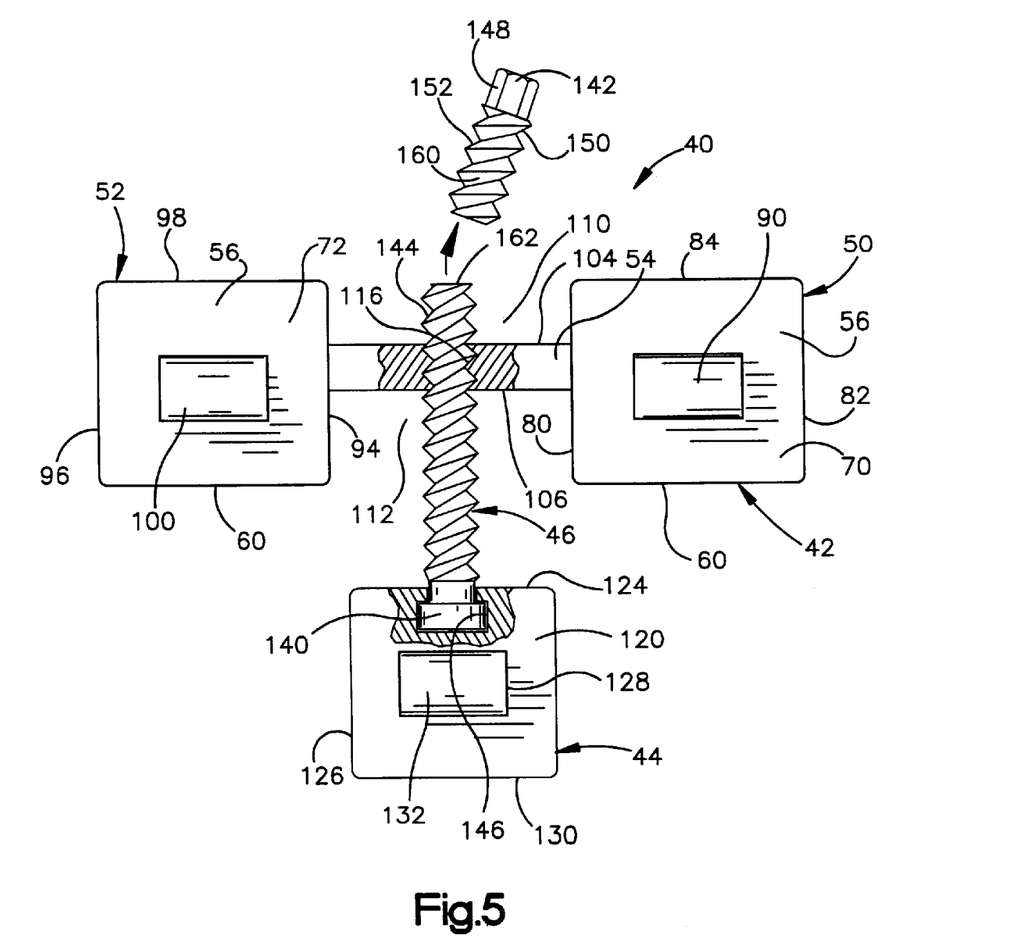
FIG. 5 is a side view taken along line 5—5 in FIG. 4.

The bridge section 54 of the first member 42 extends between the inner surface 80 of the first section 50 and the inner surface 94 of the second section 52. The bridge section 54 includes generally parallel upper and lower surfaces 104 and 106 (FIG. 5). The upper surface 104 of the bridge section 54 lies below, as viewed in the Figures, the upper surfaces 84 and 98 of the first and second sections 50 and 52, respectively of the first member 42, and defines a first recess 110 in the first member. The lower surface 106 of the bridge section 54 lies well above the arcuate end surfaces 60 of the first and second sections 50 and 52 of the first member 42 and defines a second recess 112 in the first member. The bridge section 54 of the first member further includes an axial opening 114 that extends between the upper and lower surfaces 104 and 106. The opening 114 (FIG. 3) is centered on the axis 48 and includes internal threads 116 (FIG. 5).

The second member 44 resembles each of the first and second sections 50 and 52 of the first member 42, but is slightly dimensionally smaller than the first and second sections. The second member 44 has a wedge shape defined by first and second surfaces 120 and 122 (FIG. 3) that extend at diverging angles relative to the axis 48. The first and second surfaces 120 and 122 on each of the first and second sections 50 and 52 of the second member 44 are joined by an arcuate end surface 124 that faces the bridge section 54 of the first member 42.

The second member 44 is further defined by generally parallel first and second side surfaces 126 and 128 (FIG. 5) and a generally planar lower end surface 130 that extend between the first and second surfaces 120 and 122. The lower end surface 130 is disposed opposite the arcuate end surface 124. The second member 44 further includes a first tooth 132 that projects radially outward from the first surface and a second tooth 134 (FIG. 2) that projects radially outward from the second surface 122.

The shaft member 46 projects from the arcuate end surface 124 of the second member 44 and is attached to the second member. The shaft member 44 includes oppositely disposed first and second ends 140 and 142 (FIG. 5) and a main body portion 144 that extends between the ends. The first end 140 of the shaft member is captured within a cavity 146 in the second member 44 and is supported for rotation within the cavity. The second end 142 of the shaft member 44 has a hexagonal outer surface 148 for receiving a tool (not shown) for rotating the shaft member. The main body portion 144 of the shaft member 46 has an outer surface 150 that includes external threads 152 for mating with the internal threads 116 in the opening 114 through the bridge section 54 of the first member 40.

To re-attach the cranial flap 20 to the skull 10, the cranial flap is placed in the opening in the skull in the same orientation that the cranial flap was in when the cranial flap was removed from the opening. A plurality of the attachment devices 40 are then placed in the kerf 22 between the skull 10 and the cranial flap 20 in the position illustrated in FIG. 3. The attachment devices 40 may be inserted through one of the burr holes 12 and then slid laterally into their desired locations. It should be understood that some lateral movement of the cranial flap 20 within the opening may be necessary in order to position several of the attachment devices 40 about the periphery of the cranial flap 20 as shown in FIG. 1. One or more micro-clamps (not shown) may also be inserted through the burr holes 12 and used to help align the inner and outer surfaces 30 and 28 of the cranial flap 20 with the inner and outer surfaces 34 and 32, respectively, of the skull 10. From the position of FIG. 3, each of the attachment devices 40 is operated as described below to attach the cranial flap 20 to the skull 10.

Figure 3:
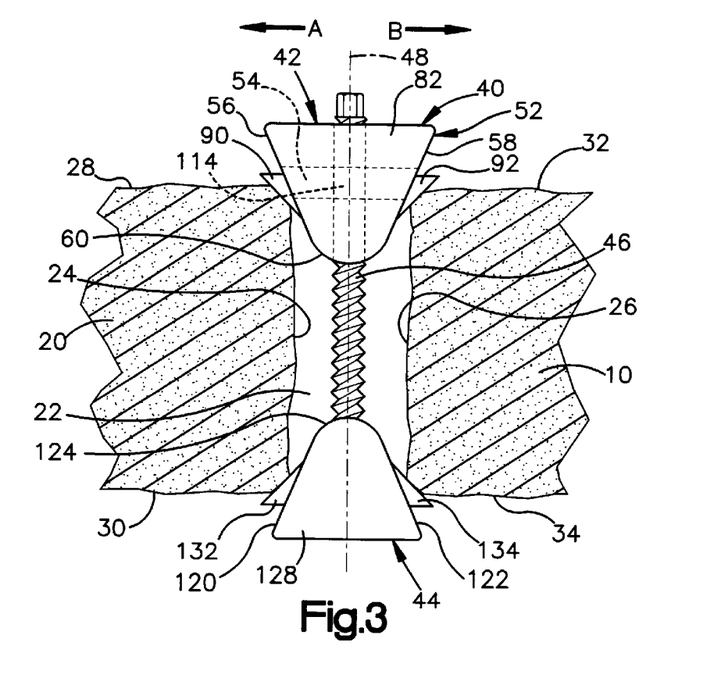
FIG. 3 is a sectional view of the apparatus taken along line 3—3 in FIG. 1 at an early stage in the attachment process.

As illustrated in FIG. 3, the first and second members 42 and 44 of the attachment device 40 are initially positioned such that the first surface 56 on the first and second sections 50 and 52 of the first member is not engaged with the first kerf edge 24 on the cranial flap 18, and such that the second surface 58 on the first and second sections of the first member is not engaged with the second kerf edge 26 on the skull 10. Likewise, in the initial condition of FIG. 3, the first surface 120 on the second member 44 is not engaged with the first kerf edge 24 on the cranial flap 20, and the second surface 122 on the second member is not engaged with the second kerf edge 26 on the skull 10.

Figure 4:
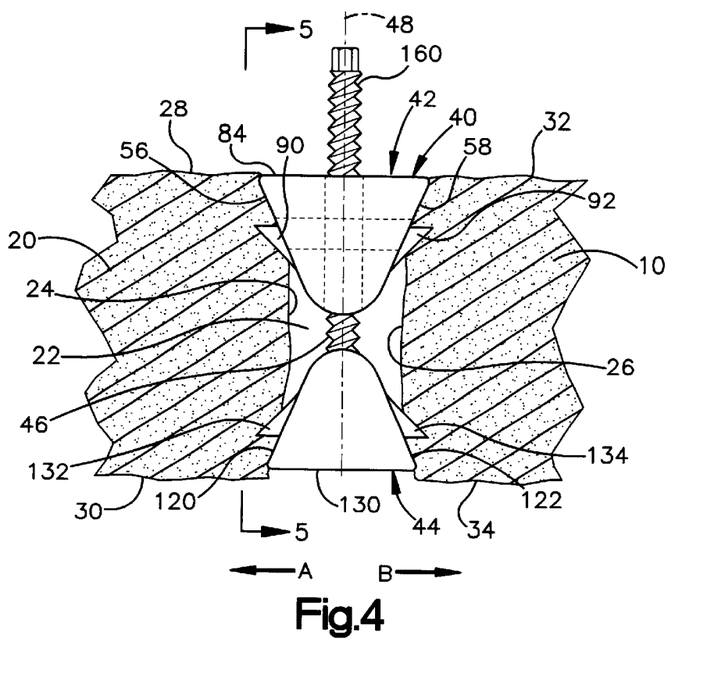
FIG. 4 is a view similar to FIG. 3 illustrating a subsequent stage in the attachment process.

The first and second members 42 and 44 of the attachment device 40 are then moved from the initial condition of FIG. 3 to a second condition illustrated in FIG. 4 by rotation of the shaft member 46. A tool (not shown) is placed on the second end 142 of the shaft member 46 to rotate the shaft member. Because the shaft member 46 can rotate relative to the second member 44 and the shaft member is threaded into the opening 114 through the bridge section 54 of the first member 42, rotation of the shaft member causes the first and second members to be drawn axially toward each other.

As the first and second members 42 and 44 are drawn toward each other, the first surface 56 on the first and second sections 50 and 52 of the first member engages the first kerf edge 24 on the cranial flap 20 and the second surface 58 on the first and second sections 50 and 52 of the first member engage the second kerf edge 26 on the skull 10. The diverging angles of the first and second surfaces 56 and 58 on the first member 42 begin to apply circumferential pressure (indicated by arrows A and B in FIGS. 3 and 4) on the first and second kerf edges 24 and 26, respectively, as the first member is drawn deeper into the kerf 22. Further, as the first member 42 moves toward the second condition shown in FIG. 4, the teeth 90 and 100 on the first surface 56 of the first member bit into the first kerf edge 24. Similarly, the teeth 92 and 102 on the second surface 58 of the first member 42 bite into the second kerf edge 26.

Likewise, as the first and second members 42 and 44 are drawn toward each other, the first surface 120 on the second member 44 engages the first kerf edge 24 on the cranial flap 20 and the second surface 122 on the second member engages the second kerf edge 26 on the skull 10. The diverging angles of the first and second surfaces 120 and 122 on the second member 44 begin to apply circumferential pressure (indicated by arrows A and B in FIGS. 3 and 4) on the first and second kerf edges 24 and 26, respectively, as the second member is drawn farther into the kerf 22. Further, as the second member 44 moves toward the second condition shown in FIG. 4, the tooth 132 on the first surface 120 of the second member bites into the first kerf edge 24. Similarly, the tooth 134 on the second surface 122 of the second member 44 bites into the second kerf edge 26.

The first and second members 42 and 44 of the attachment device 40 are drawn toward each other until the upper surfaces 84 and 98 of the first member 42 and the outer surface 28 of the cranial flap 20 are flush with the outer surface 32 of the skull 10, as shown in FIG. 4. This flush alignment of the upper surfaces 84 and 98 of the first member 42 with the outer surfaces 32 and 28 of the skull 10 and the cranial flap 20, respectively, reduces the visibility of unsightly bumps in the patient's skin (not shown) caused by the presence of the attachment device 40 underneath the skin. Accordingly, the attachment device 40 is suitable for cranial, facial, frontal, temporal, and back table applications.

When the upper surfaces 84 and 98 of the first member 42 are flush with the outer surface 32 of the skull 10, the lower surface 130 of the second member 44 is recessed slightly, as shown in FIG. 4) from the inner surface 34 of the skull 10 and the inner surface 30 of the cranial flap 20 because the second member is slightly dimensionally smaller than the first member. This helps to prevent any potentially harmful permanent contact between the second member 44 of the attachment device 40 and the dura (not shown).

As the first and second members 42 and 44 move into the second condition of FIG. 4, the first and second surfaces 56 and 58 of the first member press firmly against the first and second kerf edges 24 and 26, respectively, and wedge the first member in the kerf 22. The first member 42 is wedged in the kerf 22 by circumferential pressure and frictional engagement between the first and second surfaces 56 and 58 of the first member and the first and second kerf edges 24 and 26, respectively. Further, as the first and second members 42 and 44 move into the second condition of FIG. 4, the teeth 90 and 100 on the first and second surface 56 of the first member penetrate through the first kerf edge 24 and embed into the bone of the cranial flap 20 to establish a mechanical lock between the first member and the cranial flap. The teeth 92 and 102 on the second surface 58 of the first member 42 penetrate through the second kerf edge 26 and embed into the bone of the skull 10 to establish a mechanical lock between the first member and the skull.

Similarly, as the first and second members 42 and 44 move into the second condition of FIG. 4, the first and second surfaces 120 and 122 of the second member press firmly against the first and second kerf edges 24 and 26, respectively, and wedge the second member in the kerf 22. The second member 44 is wedged in the kerf 22 by circumferential pressure and frictional engagement between the first and second surfaces 120 and 122 of the second member and the first and second kerf edges 24 and 26, respectively. Further, the teeth 132 and 134 on the first and second surfaces 120 and 122, respectively, of the second member penetrate through the first and second kerf edges 24 and 26, respectively, and embed into the bone of the cranial flap 20 and the skull 10, respectively, to establish a mechanical interlock between the second member, the cranial flap, and the skull.

When the first and second members 42 and 44 are in the second condition illustrated in FIG. 4, an upper portion 160 of the shaft member 46 that includes the second end 142 is sheared off using a cutting tool (not shown). The first recess 104 in the first member 42 provides space for the cutting tool to access the shaft member 46 in order to shear the shaft member at a desired location. As shown in FIG. 5, the upper portion 160 of the shaft member 46 is sheared off so that a newly-formed terminal end surface 162 of the shaft member lies approximately flush with the upper surfaces 84 and 98 of the first and second sections 50 and 52, respectively, of the first member 42.

Attachment of the cranial flap 20 to the skull 10 is completed occurs when each of the attachment devices 40 spaced about the periphery of the cranial flap is moved from the first condition to the second condition as described above. The movement of each of the attachment devices 40 from the first condition to the second condition may occur simultaneously or may follow a predetermined sequence, i.e. turn each shaft member 46 one rotation at a time. When each of the attachment devices 40 has been moved to the second condition of FIG. 4, the circumferential pressure and frictional engagement between the first and second members 42 and 46 and the kerf edges 24 and 26 wedges the attachment devices in the kerf 40, thereby preventing the cranial flap 20 from moving axially or laterally relative to the skull 10. The engagement of the teeth 90, 92, 100, 102, 130 and 132 on each of the attachment devices 40 with the edges 24 and 26 of the kerf 22 aids in preventing the cranial flap 20 from moving relative to the skull 10.

Figure 6:
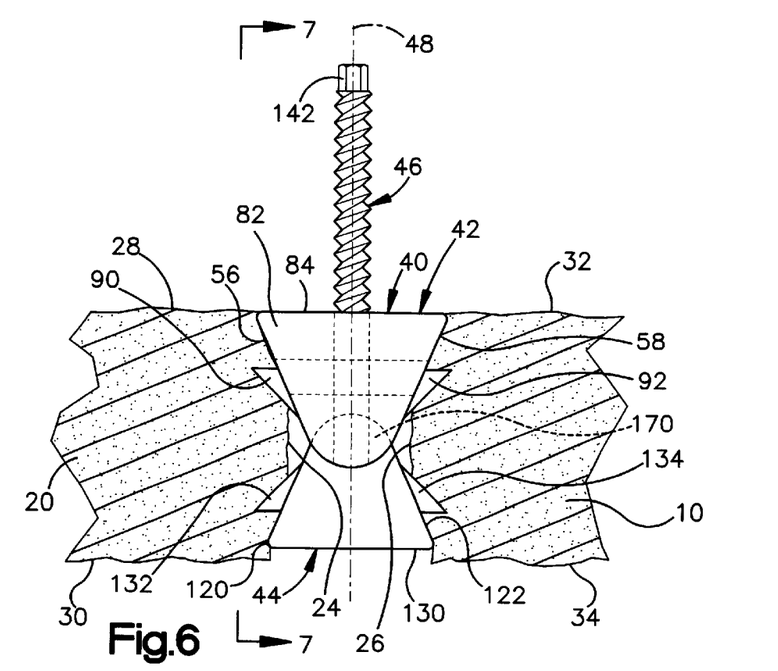
FIG. 6 is a view similar to FIG. 4 illustrating an optional further stage in the attachment process.
Figure 7:
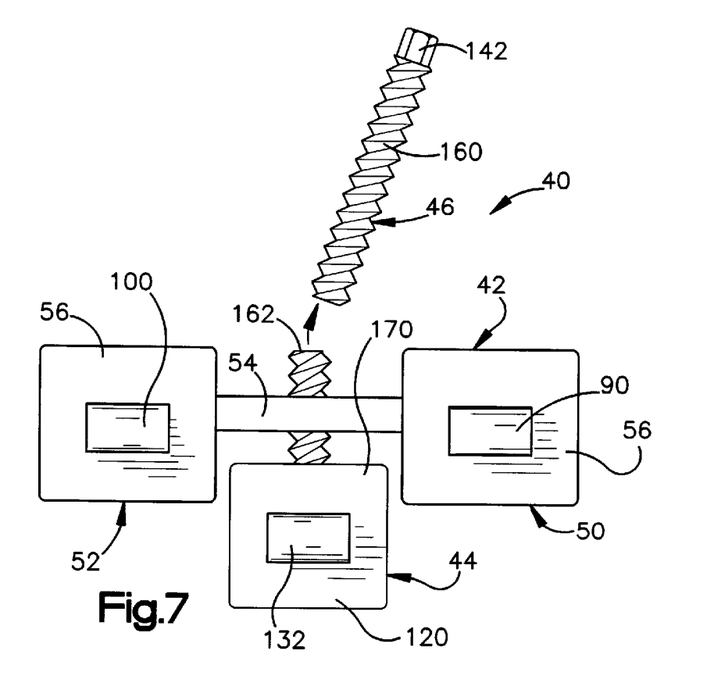
FIG. 7 is a side view taken along line 7—7 in FIG. 6.

FIGS. 6 and 7 illustrate the attachment device 40 in an optional third condition. The first and second members 42 and 44 of the attachment device 40 are moved from the second condition of FIGS. 4 and 5 to the third condition of FIGS. 6 and 7 by additional rotation of the shaft member 46 prior to shearing off the upper portion 160. In the third condition, as the first and second members 42 and 44 are drawn further together, a portion 170 of the second member moves into the second recess 112 between the first and second sections 50 and 52 of the first member. The ability of the attachment device 40 to move to the third condition allows the attachment device to adapt to smaller skull thicknesses, such as occurs with pediatric patients. As discussed previously, when the attachment device 40 has been wedged in the kerf 22 and the cranial flap 20 is secured to the skull 10, the upper portion 160 of the shaft member 46 is sheared off, as is shown schematically in FIG. 7.

Figure 8:
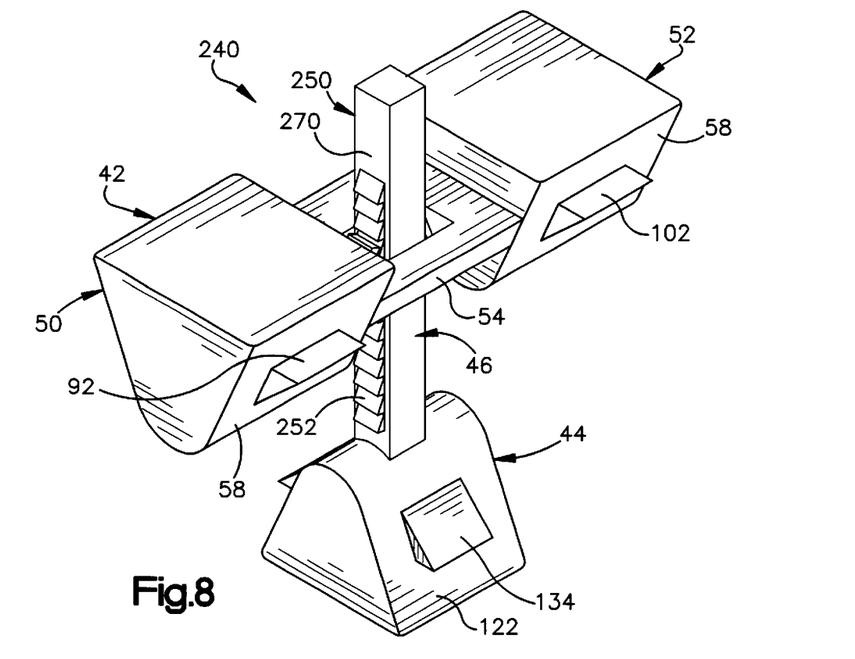
FIG. 8 is a perspective view illustrating an apparatus for attaching a cranial flap in accordance with a second embodiment of the present invention.
Figure 9:
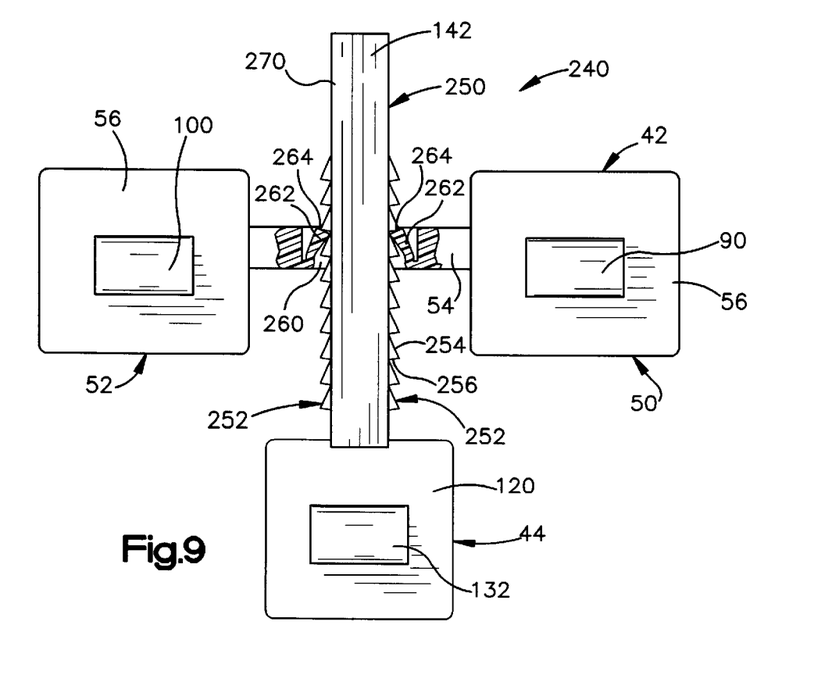
FIG. 9 is a side view of the apparatus of FIG. 8.

FIGS. 8 and 9 illustrate an attachment device constructed in accordance with a second embodiment of the present invention. In the second embodiment of FIGS. 8 and 9, reference numbers that are the same as reference numbers used in the first embodiment of FIGS. 1–7 are used to identify parts in the second embodiment that are the same as parts in the first embodiment.

According to the second embodiment, the first and second members 42 and 44 of the attachment device 240 are connected by a shaft member 250. The shaft member 250 is fixedly connected to the second member 44 and extends through an opening 260 (FIG. 9) in the bridge section 54 of the first member 42. The outer surface of the shaft member 250 includes two axially extending rows of teeth 252. The two rows of teeth 252 are disposed diametrically opposite one another. Each of the teeth 252 has a ramp surface 254 and a catch surface 256.

The opening 260 through the bridge section 54 includes a diametrically opposed pair of deflectable detents 262 for engaging the two rows of teeth 252 on the shaft member 250. Each of the detents 262 has a stop surface 264 that is engageable with the catch surface 256 on a respective one of the teeth 252 to prevent movement of the shaft member 46 away from the first member 42.

To attach the cranial flap 20 to the skull 10 using the attachment device 240 according to the second embodiment, the shaft member 46 is pulled axially through the opening 260 so that the second member 44 moves toward the first member 42. The shaft member 46 may be pulled axially using a tool (not shown) that grips the second end 142 of the shaft member. As the shaft member 46 is pulled through the opening 260, the ramp surfaces 254 on the teeth 252 deflect the detents 262 radially outward as the teeth move past the detents. The detents 262 then snap back radially inward between each of the teeth 252 so that the stop surfaces 264 on the detents 262 engage the catch surfaces 256 on the teeth. The engagement of the stop surfaces 256 on the teeth 252 and the catch surfaces 264 on the detents 262 prevents the shaft member 46 from being pulled out of the opening 260 and away from the first member 42.

As with the first embodiment, attachment of the cranial flap 20 to the skull 10 is completed when each of the attachment devices 240 spaced about the periphery of the cranial flap is moved from the first condition to the second condition, or the third condition, as described above. The movement of each of the attachment devices 240 from the first condition to the second condition may occur simultaneously or may follow a predetermined sequence, i.e. pull each shaft member 46 up one tooth 252 at a time. When each of the attachment devices 240 has been moved to the second condition, the circumferential pressure and frictional engagement between the first and second members 42 and 44 (including the teeth 90, 92, 100, 102, 130 and 132) and the kerf edges 24 and 26 wedges the attachment devices in the kerf 22, thereby preventing the cranial flap 20 from moving axially or laterally relative to the skull 10. As with the first embodiment, when each of the attachment devices 240 have been wedged in the kerf 22 and the cranial flap 20 is secured to the skull 10, an upper portion 270 of the shaft member 46 is sheared off.

The attachment devices 40 and 240 disclosed above eliminate the use of screws in the re-attachment process, which reduces the amount of time needed by the surgeon to complete the re-attachment of the cranial flap 20. Further, the attachment devices 40 and 240 are disposed entirely within the kerf 22 and thus do not permanently contact the dura, nor do the attachment devices protrude beyond the outer surface 32 of the skull 10 which could result in unsightly bumps in the patient's skin. Finally, the attachment devices 40 and 240 are advantageously adaptable to a wide range of skull thicknesses.

From the above description of the invention, those skilled in the art will perceive improvements, changes and modifications. Such improvements, changes and modifications within the skill of the art are intended to be covered by the appended claims.

Having described the invention, we claim:

1. An apparatus for attaching a cranial flap to a skull during surgery, the cranial flap and the skull being spaced apart by a kerf defined by a first kerf edge on the cranial flap and an oppositely disposed second kerf edge on the skull, said apparatus comprising:

at leapt one attachment device comprising relatively movable first and second members, said first and second members being movable relative to each other along an axis;

said first member having oppositely disposed first and second surfaces for engaging the first and second kerf edges, respectively, said first member further including an opening extending along said axis;

said second member having oppositely disposed third and fourth surfaces for engaging the first and second kerf edges, respectively; and a shaft member connecting said first and second members, said shaft member being attached to said second member and extending through said opening in said first member;

said at least one attachment device being positionable in the kerf and movable from a first condition in which said first surface on said first member and said third surface on said second member are not engaged with the first kerf edge and the second surface on said first member and said fourth surface for said second member are not engaged with the second kerf edge to a second condition in which said at least one attachment device is wedged in the kerf by circumferential pressure and frictional engagement between said first and third surfaces arid the first kerf edge and by circumferential pressure and frictional engagement between said second and fourth surfaces and the second kerf edge to thereby attach the cranial flap to the skull and prevent the cranial flap from moving relative to the skull;

wherein relative movement between said first and second members draws said members toward each other along said axis.

2. The apparatus of claim 1 wherein said second member has a wedge shape defined by said third and fourth surfaces extending at diverging angles relative to said axis.

3. The apparatus of claim 1 wherein said third surface of said second member includes at least one radially extending extending tooth for penetrating through the first kerf edge and into the cranial flap and said fourth surface of said second member includes at least one radially extending extending tooth for penetrating through the second kerf edge and into the skull.

4. The apparatus of claim 1 wherein said at least one attachment device comprises a plurality of attachment devices positioned in the kerf and spaced apart around the periphery of the cranial flap.

5. The apparatus of claim 1 wherein said shaft member is supported for rotation relative to said second member and has an outer surface that includes external threads.

6. The apparatus of claim 5 wherein said opening in said first member includes internal threads, said second member being movable relative to said first member by rotation of said shaft member.

7. The apparatus of claim 1 wherein said first member has first and second sections connected by a bridge portion, said opening being disposed in said bridge portion.

8. An apparatus for attaching a cranial flap to a skull during surgery, the cranial flap and the skull being spaced apart by a kerf defined by a first kerf edge on the cranial flap and an oppositely disposed second kerf edge on the skull, said apparatus comprising:

at least one attachment device comprising relatively movable first and second members, said first and second members being movable relative to each other along an axis;

said first member having a wedge shape defined by said first and second surfaces extending at diverging angles relative to said axis, said first and second surfaces for engaging the first and second kerf edges, respectively, said first member further including an opening extending along said axis;

said second member having a wedge shape defined by said third and fourth surfaces extending at diverging angles relative to said axis, said third and fourth surfaces for engaging the first and second kerf edges, respectively; and a shaft member connecting said first and second members, said shaft member being attached to said second member and extending through said opening in said first member;

said at least one attachment device being positionable in the kerf and movable from a first condition in which said first surface on said first member and said third surface on said second member are not engaged with the first kerf edge and the second surface on said first member and said fourth surface on said second member are not engaged with the second kerf edge to a second condition in which said at least one attachment device is wedged in the kerf by circumferential pressure and frictional engagement between said first and third surfaces and the first kerf edge and by circumferential pressure and frictional engagement between said second and fourth surfaces and the second kerf edge to thereby attach the cranial flap to the skull and prevent the cranial flap from moving relative to the skull, said at least one attachment device in said second condition being disposed entirely within the kerf;

said at least one attachment device being movable from said first condition to said second condition by axial movement of at least one said first and second members toward the other of said first and second members.

9. An apparatus for attaching a cranial flap to a skull during surgery, the cranial flap and the skull being spaced apart by a kerf defined by a first kerf edge on the cranial flap and an oppositely disposed second kerf edge on the skull, said apparatus comprising:

at least one attachment device comprising relatively movable first and second members, said first and second members being movable relative to each other along an axis;

said first member having oppositely disposed first and second surfaces for engaging the first and second kerf edges, respectively, said first member further including an opening extending along said axis;

said second member having oppositely disposed third and fourth surfaces for engaging the first and second kerf edges, respectively; and a shaft member connecting said first and second members, said shaft member being attached to said second member and extending through said opening in said first member;

said at least one attachment device being positionable in the kerf and movable from a first condition in which said first surface on said first member and said third surface on said second member are not engaged with the first kerf edge and the second surface on said first member and said fourth surface on said second member are not engaged with the second kerf edge to a second condition in which said at least one attachment device is wedged in the kerf by circumferential pressure and frictional engagement between said first and third surfaces and the first kerf edge and by circumferential pressure and frictional engagement between said second and fourth surfaces and the second kerf edge to thereby attach the cranial flap to the skull and prevent the cranial flap from moving relative to the skull;

wherein movement of said at least one attachment device from said first condition to said second condition is accomplished by axial movement of at least one said first and second members toward the other of said first and second members.

10. An apparatus for attaching a cranial flap to a skull during surgery, the cranial flap and the skull being spaced apart by a kerf defined by a first kerf edge on the cranial flap and an oppositely disposed second kerf edge on the skull, said apparatus comprising:

at least one attachment device comprising relatively movable first and second members, said first and second members being movable relative to each other along an axis;

said first member having oppositely disposed first and second surfaces for engaging the first and second kerf edges, respectively, said first member further including an opening extending along said axis;

said second member having oppositely disposed third and fourth surfaces for engaging the first and second kerf edges, respectively; and a shaft member connecting said first and second members, said shaft member being attached to said second member and extending through said opening in said first member;

said at least one attachment device being positionable in the kerf and movable from a first condition in which said first surface on said first member and said third surface on said second member are not engaged with the first kerf edge and the second surface on said first member and said fourth surface on said second member are not engaged with the second kerf edge to a second condition in which said at least one attachment device is wedged in the kerf by circumferential pressure and frictional engagement between said first and third surfaces and the first kerf edge and by circumferential pressure and frictional engagement between said second and fourth surfaces and the second kerf edge to thereby attach the cranial flap to the skull and prevent the cranial flap from moving relative to the skull;

said first member having a wedge shape defined by said first and second surfaces extending at diverging angles relative to said axis.

11. An apparatus for attaching a cranial flap to a skull during surgery, the cranial flap and the skull being spaced apart by a kerf defined by a first kerf edge on the cranial flap and an oppositely disposed second kerf edge on the skull, said apparatus comprising:

at least one attachment device comprising relatively movable first and second members, said first and second members being movable relative to each other along an axis;

said first member having oppositely disposed first and second surfaces for engaging the first and second kerf edges, respectively, said first member further including an opening extending along said axis;

said second member having oppositely disposed third and fourth surfaces for engaging the first and second kerf edges, respectively; and a shaft member connecting said first and second members, said shaft member being attached to said second member and extending through said opening in said first member;

said at least one attachment device being positionable in the kerf and movable from a first condition in which said first surface on said first member and said third surface on said second member are not engaged with the first kerf edge and the second surface on said first member and said fourth surface on said second member are not engaged with the second kerf edge to a second condition in which said at least one attachment device is wedged in the kerf by circumferential pressure and frictional engagement between said first and third surfaces and the first kerf edge and by circumferential pressure and frictional engagement between said second and fourth surfaces and the second kerf edge to thereby attach the cranial flap to the skull and prevent the cranial flap from moving relative to the skull;

wherein said first surface of said first member including at least one radially extending extending tooth for penetrating through the first kerf edge and into the cranial flap, said second surface of said first member including at least one radially extending extending tooth for penetrating through the second kerf edge and into the skull.

12. An apparatus for attaching a cranial flap to a skull during surgery, the cranial flap and the skull being spaced apart by a kerf defined by a first kerf edge on the cranial flap and an oppositely disposed second kerf edge on the skull, said apparatus comprising:

at least one attachment device comprising relatively movable first and second members, said first and second members being movable relative to each other along an axis;

said first member having oppositely disposed first and second surfaces for engaging the first and second kerf edges, respectively, said first member further including an opening extending along said axis;

said second member having oppositely disposed third and fourth surfaces for engaging the first and second kerf edges, respectively; and a shaft member connecting said first and second members, said shaft member being attached to said second member and extending through said opening in said first member;

said at least one attachment device being positionable in the kerf and movable from a first condition in which said first surface on said first member and said third surface on said second member are not engaged with the first kerf edge and the second surface on said first member and said fourth surface on said second member are not engaged with the second kerf edge to a second condition in which said at least one attachment device is wedged in the kerf by circumferential pressure and frictional engagement between said first and third surfaces and the first kerf edge and by circumferential pressure and frictional engagement between said second and fourth surfaces and the second kerf edge to thereby attach the cranial flap to the skull and prevent the cranial flap from moving relative to the skull;

said shaft member having an outer surface that includes at least one row of teeth, said opening in said first member having at least one detent that engages said at least one row of teeth, the engagement of said at least one detent in said at least one row of teeth permitting said second member to move axially toward said first member and preventing said second member from moving away from said first member.

13. An apparatus for attaching a cranial flap to a skull during surgery, the cranial flap and the skull being spaced apart by a kerf defined by a first kerf edge on the cranial flap and an oppositely disposed second kerf edge on the skull, said apparatus comprising:

at least one attachment device comprising relatively movable first and second members, said first and second members being movable relative to each other along an axis;

said first member having oppositely disposed first and second surfaces for engaging the first and second kerf edges, respectively, said first member further including an opening extending along said axis;

said second member having oppositely disposed third and fourth surfaces for engaging the first and second kerf edges, respectively; and a shaft member connecting said first and second members, said shaft member being attached to said second member and extending through said opening in said first member;

said at least one attachment device being positionable in the kerf and movable from a first condition in which said first surface on said first member and said third surface on said second member are not engaged with the first kerf edge and the second surface on said first member and said fourth surface on said second member are not engaged with the second kerf edge to a second condition in which said at least one attachment device is wedged in the kerf by circumferential pressure and frictional engagement between said first and third surfaces and the first kerf edge and by circumferential pressure and frictional engagement between said second and fourth surfaces and the second kerf edge to thereby attach the cranial flap to the skull and prevent the cranial flap from moving relative to the skull;

said first member having first and second sections connected by a bridge portion, said opening being disposed in said bridge portion;

said second member being movable to a position in which a portion of said second member is disposed between said first and second sections of said first member.

14. The apparatus of claim 13 wherein said first surface on said first member includes a first portion that extends across said first section of said first member and a second portion that extends across said second section of said first member, said second surface on said first member including a second portion that extends across said first section of said first member and a second portion that extends across said second section of said first member.

15. The apparatus of claim 14 wherein each of said first and second portions of said first surface of said first member includes at least one radially extending extending tooth for penetrating through the first kerf edge and into the cranial flap and each of said first and second portions of said second surface of said first member includes at least one radially extending extending tooth for penetrating through the second kerf edge and into the skull.

16. An apparatus for attaching a cranial flap to a skull during surgery, the cranial flap and the skull being spaced apart by a kerf defined by a first kerf edge on the cranial flap and an oppositely disposed second kerf edge on the skull, said apparatus comprising:

at least one attachment device comprising relatively movable first and second members, said first and second members being movable relative to each other along an axis;

said first member having oppositely disposed first and second surfaces for engaging the first and second kerf edges, respectively, said first member further including an opening extending along said axis;

said second member having oppositely disposed third and fourth surfaces for engaging the first and second kerf edges, respectively; and a shaft member connecting said first and second members, said shaft member being attached to said second member and extending through said opening in said first member;

said at least one attachment device being positionable in the kerf and movable from a first condition in which said first surface on said first member and said third surface on said second member are not engaged with the first kerf edge and the second surface on said first member and said fourth surface on said second member are not engaged with the second kerf edge to a second condition in which said at least one attachment device is wedged in the kerf by circumferential pressure and frictional engagement between said first and third surfaces and the first kerf edge and by circumferential pressure and frictional engagement between said second and fourth surfaces and the second kerf edge to thereby attach the cranial flap to the skull and prevent the cranial flap from moving relative to the skull;

said at least one attachment device in said second condition, being disposed entirely within the kerf and not engaged with any other surfaces on the skull or the cranial flap.

* * * * *